United States Patent [19]

Sang et al.

[11] Patent Number: 5,039,559
[45] Date of Patent: Aug. 13, 1991

[54] METHOD OF MAKING MAGNETICALLY ATTRACTABLE PARTICLES

[76] Inventors: Jean V. Sang, 4404 Bath Road, Kingston, Ontario, Canada, K7N 1A2; Paul Groves, Flat 5, Sandford Mount, Charlbury, Oxon, England; Robert E. Burrell, 187 Chelsea Road, Kingston, Ontario, Canada, K7M 3Z1; Gerard Flynn, Home Farm Cottage, Barford Road, Bloxham, Oxon, England

[21] Appl. No.: 440,500

[22] Filed: Nov. 22, 1989

Related U.S. Application Data

[63] Continuation of Ser. No. 355,651, May 22, 1989, abandoned.

[30] Foreign Application Priority Data

May 24, 1988 [GB] United Kingdom ............... 8812218
Jun. 20, 1988 [CA] Canada ............................ 569920

[51] Int. Cl.$^5$ .................. B01J 13/02; C04B 35/26; C04B 35/64; H01F 1/36
[52] U.S. Cl. .................. 427/213.3; 106/457; 106/459; 252/62.56; 252/62.61; 252/309; 427/127; 428/402.24; 435/176; 501/12
[58] Field of Search ............... 427/213.3, 127; 106/457, 459; 252/62.56; 435/176; 252/62.61; 501/12

[56] References Cited

U.S. PATENT DOCUMENTS

| | | | |
|---|---|---|---|
| 1,669,647 | 5/1928 | Bandur | 427/127 X |
| 3,954,678 | 5/1976 | Marquisee | 252/62.56 X |
| 4,011,096 | 3/1977 | Sandell | 106/300 X |
| 4,115,534 | 9/1978 | Ithakissios | 427/213.3 X |
| 4,309,459 | 1/1982 | Tokuoka | 427/127 X |
| 4,343,901 | 8/1982 | DeFilippi | 435/176 |
| 4,438,156 | 3/1984 | Homola et al. | 427/127 X |
| 4,461,832 | 7/1984 | Tschang et al. | 427/213.3 X |
| 4,882,224 | 11/1989 | Moro et al. | 427/127 X |

Primary Examiner—Richard D. Lovering
Attorney, Agent, or Firm—Cooper & Dunham

[57] ABSTRACT

Magnetically attractable particles comprise a core of magnetic material encapsulated in a metal oxide coating. They may be made by emulsifying an aqueous solution or dispersion of the magnetic material or precursor, and an aqueous solution or sol of a coating inorganic oxide or precursor, in an inert water-immiscible liquid. The aqueous droplets are gelled, e.g. by ammonia or an amine., recoverd, and heated at 250°–2000° C. The resulting particles are generally smooth spheres below 100 microns in diameter and often of sub-micron size.

11 Claims, No Drawings

METHOD OF MAKING MAGNETICALLY ATTRACTABLE PARTICLES

CROSS-REFERENCE TO RELATED APPLICATION

This application is a continuation of applicants' co-pending U.S. Pat. application Ser. No. 355,651, filed May 22, 1989, and now abandoned.

This invention concerns a method of making magnetically attractable particles, which are suitable for use in biological separations. There is an established market for such products.

BACKGROUND OF THE INVENTION

A variety of techniques have been developed for the production of ceramic particles which involve the precipitation of a precursor of the powder from an aqueous solution containing the desired cations of the ceramic. In many of these techniques, the solution is mixed with a reagent which will precipitate the cations in the form of easily reducible compounds, such as hydroxides, carbonates, oxalate, etc. The precipitates are separated from the liquid and sintered to reduce them to the respective oxides. A technique, which is particularly advantageous in developing ceramic particles in the micrometer size or less, is disclosed in co-pending Canadian patent application Serial Number 544868-9, filed 19 Aug. 1987 of which one of the two inventors is also co-inventor of this application.

Other techniques for preparing ceramic powders are disclosed in French patent 2,054,131. The patent disclosed the emulsification of an aqueous solution of the metallic salts which form the ceramic. The emulsion is treated to remove the liquid and calcine the resultant solid phase to produce the ceramic particles.

Considerable attention has also been given to the development of micron size particles for use in biological treatments. A particular area of interest is the development of magnetic particles agglomerated or individually coated with materials to which biological substances can adhere. Examples of magnetic particles for use in this manner are disclosed in U.S. Pat. Nos. 3,330,693; 4,152,210 and 4,343,901. European Patent application 176,638 published Apr. 9, 1986 also discloses the use of magnetic particles for the immobilization of biological protein. Several of these patents contemplate coating of the magnetic core with a polymeric material, or agglomerating several particles in a suitable polymer such as disclosed in U.S. Pat. No. 4,343,90.

The use for magnetic materials in the biological field continues to increase, hence an increased demand for superior materials. Consider, for example, the use of such particles for immobilizing enzymes or antibodies. Separation of such materials from other non-magnetic solids by the use of a magnetic field permits separations and concentrations which would be otherwise difficult or even impossible to perform. Besides allowing separation of the support from suspended solids in the process liquids, the ease and power of magnetic collection permits the use of very small support particles. In turn, this allows the use on non-porous particles, while still retaining a reasonable specific area for enzymes or antibodies. Another advantage of such magnetic materials is their potential use in a magnetic stabilized fluid bed, thereby presenting further options in continuous reactor systems.

From the noted patents, a variety of magnetic materials have been used in the preparation of magnetic supports matrices including iron, nickel, cobalt, and their oxides as well as composite materials such as ferrites. However, such supports suffer from some disadvantages. First, metal ions from uncoated metal or metal oxide surfaces may irreversibly inhibit some enzymes, particularly when the enzyme is attached directly to the metal surface. Methods have been devised to attach the enzyme to the inorganic material with the aid of intermediate crosslinking agents and/or to coat the magnetic material with organic coatings as noted in U.S. Pat. No. 4,152,210.

Coating of magnetic material with inorganic coatings has also been proposed. U.S. Pat. No. 4,343,901 describes a magnetic support matrix comprising a porous refractory inorganic oxide, through the interior of which are dispersed particles from about 0.05 micron to about 0.5 millimeter of ferromagnetic materials, said oxide being impregnated with a polyamine cross-linked with an excess of a bi-functional reagent so as to furnish pendent functional groups. The refractory inorganic oxide, which may be obtained by a sol-gel technique, is calcined before use. Ferro-magnetic materials above 0.05 micron in size are not superparamagnetic and therefore exhibit permanent residual magnetism. Furthermore, the coatings proposed do not appear to be continuous and as a result would not prevent losses in enzyme activity.

Coated magnetic particles have been also devised for various alternative uses. GB 2064502 describes a method of making coated magnetic particles, for use in ion-exchange resins, filter aids or absorbents, by precipitating chromium hydrogel onto magnetic particles from 0.05 to 5 microns in diameter and which are therefore not superpara-magnetic. The proportion by weight of magnetic particles in the coated magnetic particles is at least 50%, generally 90 to 98%.

JP-A-6364308 describes magnetic fluids containing permanently suspended particles comprising ferromagnetic material dispersed in a heat-resistant inorganic oxide.

SUMMARY OF THE INVENTION

In one aspect this invention provides a method of making magnetically attractable particles by the use of:
 a) a precursor salt solution or sol or dispersion of magnetic material,
 b) a precursor salt solution or sol of a coating inorganic oxide, and
 c) an inert liquid immiscible with the solvent used in a) and b),
 which method comprises emulsifying a) and b) either together or separately in c), converting droplets of the emusion to a gel, and heating the resulting gel droplets to form magnetically attractable particles comprising the magnetic material encapsulated in the coating inorganic oxide.

In another aspect, the present invention provides water-dispersable magnetically attractable particles comprising a mass of finely divided superpara-magnetic material or "soft" magnetic material or low-Curie point magnetic material encapsulated in an inorganic oxide or hydrated oxide formed by a gel technique, the particles having the property of being readily brought down out of dispersion by application of a magnetic field and of being readily re-dispersed after removal of the magnetic field.

In yet another aspect the invention provides a coated ferromagnetic particle having a diameter in the range of 0.1 to 100 micrometers and comprising a discrete core of magnetic material coated with a metal oxide selected from the group consisting of $Al_2O_3$, $SiO_2$, $TiO_2$, $ZrO_2$, hydroxy-apatite and mixtures thereof, said coating weighing in the range of 1% to 95% of said core weight and providing a continuous coating over the entire surface of said core to prevent exposure of said core to surrounding media.

DETAILED DESCRIPTION OF THE INVENTION RECORD

Component a) is a precursor salt solution or dispersion of magnetic material. A precursor salt solution may be a mixture of salts in proportion chosen to give rise, on heating, to the desired magnetic material.

The magnetic material can be either one which would form superparamagnetic particles or one made of a soft magnetic material or one made of a low Curie point magnetic material. Superparamagnetism is characterized by the absence of any measurable permanent magnetization. Superparamagnetism is typically exhibited by magnetic particles with particle size less than about 30 nm. Superparamagnetic materials are available commercially or may readily be made by known techniques. Soft magnetic materials are those that react quickly to changes in magnetic fields and are characterized by a low permanent magnetization. Soft magnetic materials include a variety of so-called ferrites such as nickel zinc ferrite. Particles incorporating either superparamagnetic or soft magnetic materials have the great advantage of being, not only readily attractable out of dispersion by application of a magnetic field, but also readily re-dispersable when the magnetic field is removed. Finally, particles with magnetic cores having low Curie temperatures can also be readily redispersed after exposure to magnetic fields by heating above such a temperature at which permanent magnetization is lost. There are many magnetic materials exhibiting low Curie temperatures such as aluminum-substituted nickel ferrites, e.g. nickel ferro-aluminates $NiFe_{2-2xo}Al_{2x}O_4$ which may have Curie temperatures below 100° C. for $X = 0.8$.

Component b) can be formed of a variety of inorganic oxide or hydrated oxide materials, which may include $Al_2O_3$, $TiO_2$, $ZrO_2$, $Cr_2O_3$, $Fe_2O_3$, $CeO_2$, $In_2O_3$, $Ga_2O_3$ $SiO_2$ or mixtures thereof or composites such as hydroxy-apatite. These are preferably derived from aqueous colloidal dispersions (sols) but may also be organic based, e.g. derived from metal alkoxides. Colloidal sols can be developed in accordance with well known processing techniques. For example, a solution of the metal salt may be neutralized with aqueous ammonia, aged and then peptized with nitric acid to a pH of approximately 2 to form colloids having a particle size in the range of 10–50 nm. The starting colloidal or alkoxide sol may also contain various other components, for example, water soluble salts to tailor the composition and properties in the manner desired. Compositions may include, for example, biocompatible glasses or hydroxy-apatites. Mixtures of sols can also be used in order to give the required composite properties. Reactive species may also be incorporated, to provide surface sites for subsequent binding to components, e.g. enzymes or substrates therefor, of biological systems. Surface active agents may be included to provide well-shaped gel particles.

In another approach, a metal salt solution may be used in place of the sol.

These techniques permit a substantial degree of control over the chemistry of the resulting particles. For example, use of sols or solutions based on $ZrO_2$ or $TiO_2$ was found to give rise to particles having excellent resistance to degradation and leaching of encapsulated material. Use of sols or solutions based on $SiO_2$ or $Fe_2O_3$ was also found to give rise to particles that may have lower resistance to degradation and leaching, but which have numerous reactive sites for binding to molecules of biological interest. Use of mixed sols and solutions can give rise to particles having a desired combination of resistance to degradation and leaching and biologically reactive sites. Incorporation of a powder passenger, e.g. of a refractory metal oxide, in the sol or solution may be useful in order to increase the specific surface area of the particles and thus increase the number of sites available for binding to molecules of biological interest. Particulate non-magnetic refractory oxide material for this purpose may typically have a particle size from 0.1 to 10 microns (but always less than the size of the water-dispersable particles), and may typically be present in a proportion of up to 40% by weight.

Component c) is an inert liquid immiscible in the solvents used in a) and b). This is used as the continuous phase of an emulsion and its nature is not very critical. Suitable liquids include chlorinated hydrocarbons such as i,i,i-trichloroethane, paraffin oil, and hydrocarbons such as hexane, heptane, octane and toluene. The art of preparing emulsions is well understood so that the selection of a suitable inert liquid is fully appreciated by those skilled in the art.

The first step of the method involves emulsifying components a) and b) in c). In one embodiment, finely divided magnetic material, in the form of a precipitate or aqueous dispersion, is dispersed throughout the solution or sol b) and the resulting mixture is then emulsified in the immiscible liquid c). In another embodiment, components a) and b) are separately emulsified in component c), either at the same time or at different times as described below.

The emulsion of particles is developed to produce droplets of chosen size which may be less than 100 micrometers and preferably less than 5 micrometers. To promote the development of the emulsion, it is preferable to include a suitable surfactant. Surfactants also lend stability to the emulsion once the desired droplet size has been developed. Surfactants are often classified by the ratio of the hydrophilic-lipophilic balance (HLB) number. HLB numbers are determined empirically and range from i to 40. Surfactants having HLB numbers; i.e. Less than 10, are considered to be hydrophobic emulsifiers to form water in oil emulsions. Hence for the preparation of the emulsion, suitable hydrophobic emulsifiers having HLB numbers Less than 10, such as sorbitan monoleate or Span 80 (ICI, UK) are used.

The solutions, in this technique, can be made for example by using distilled water of the purity required to avoid introduction of unwanted cations, the wanted cations being introduced in the form of suitable water soluble salts, e.g. nitrates, carbonates, acetates, etc. The fraction of the solution can be theoretically as high as 74% by volume which corresponds to the theoretical maximum volume that can be occupied by closely packed, uniform spherical particles. In practice, however, it is preferred to use a smaller fraction of about 30% to 50% by volume, since higher concentrations result in distortion from the spherical shape of the dispersed phase leading to non-uniformity in size of the resultant coated particles.

The next step comprises treating the developed emulsion with a suitable reactant to gel the previously formed droplets. This is usually done by a change In pH. Such a change of pH should take place without breaking of the emulsion so that unformity and discreteness of the developed droplets s maintained. Such change in pH can be accomplished by bubbling ammonia through the emulsion or introducing ammonium hydroxide or a liquid amine, such as ethanolamine or hexamethylene diamine, into the emulsion. Other useful gases include $CO_2$ which may be bubbled through the solution.

The objective, however, of this aspect of the method is to coat the particles developed in the above process steps. Depending upon when the coating composition is introduced to the above steps, a variation in particle size and shape can be achieved.

According to an aspect of the method, the colloidal particles of the coating metal oxide may be added to the aqueous solution of salts of the metal ions of component a) prior to emulsification. In that case, the finely dispersed solids added to the salt solution stabilize the emulsion and as a result, very fine particles of the order of 1 micrometer can be obtained. This phenomenon of stabilization of emulsion by finely dispersed solids is well known. In this situation, the surface of the colloid can be modified by the controled absorption of some surface active agents, such as sodium dodecyl sulfate, HLB greater than 10, which make the particles hydrophobic and therefore preferentially wettable by the oil phase.

The coating material b) can also be introduced at a later stage. In that instance, the coating material can be in the form of colloids suspended in an aqueous solution or in the form of an aqueous solution containing the respective cation or mixture of cations. Wetting of the emulsion droplets by such coatings is preferred by rendering the droplet surface hydrophilic. This is achieved by the addition of a surfactant having a high HLB value, for example, aliphatic polyethers, such as Antarox CO 530TM having an HLB number of 10.8. or G1045 of HLB number of 11.5 or Tween 80 of HLB number of 15 or also mixes of surfactants such as Tween 80 or Span 80 adjusted in proportion to obtain a suitable HLB number preferably between 11 and 14. Dispersion of the emulsion droplets in the coating solution is achieved by an emulsifier. Such an emulsification produces a multiple emulsion i.e. a water in oil in water emulsion usually noted as w/o/w/ emulsion. It was found that such a multiple emulsion was more stable and therefore that the coating was more uniform when (i) the emulsion droplets were washed by displacement washings with the oil phase. Such washings were required to remove the excess amount of micelles created in the first emulsification step, and (ii) the amount of oil left with the emulsion droplets was minimum.

Coating thickness can be adjusted by re-emulsifying the dispersion to produce a second emulsion using the previously noted Sorbitan monooleate surfactant in the non-miscible solvent such as n-heptane.

According to another aspect of the process, after the coating material is introduced in the form of a solution, the second emulsion may be reacted with a suitable reactant as previously indicated to precipitate the coated ceramic particles.

In biological applications, it is apparent that with the minute particles it is essential that each particle be completely coated with an inert metal oxide to avoid contamination of the biological media with the inner potentially toxic core which normally has some form of magnetic property.

The gel particles may be de-watered by conventional means and are thereafter recovered from the emulsion. The gel particles are heated, if necessary to convert to oxide or hydrated oxide. This may typically involve heating at 250 to 2000° C. The resulting particles are typically from 0.1 to 100 microns in diameter, and comprise magnetic material encapsulated in a metal oxide coating, the weight ratio of magnetic material to coating being from 1.99 to 95:5. The particles may be irregular, but are often spherical. Different preparative processes give rise to particles having different characteristics:

Methods which involve first dispersing ferro-magnetic materials in an aqueous sol of a coating inorganic oxide. The particles typically have a magnetic material content below 50% e.g. from 1 to 40% by weight. They are typically spherical with an average size preferably from 0.5 to 10 microns. They comprise a mass of finely divided magnetic material encapsulated within the coating. It might have been supposed that the magnetic material would be uniformly distributed through the particle with a significant proportion accessible to reagents at the surface. This is surprisingly found not to be the case. The ferro-magnetic material is substantially encapsulated with little or none, typically Less than 10%, of the material accessible at the surface. This is so, even when steps are deliberately taken to make the particles to some extent porous. It is an advantage that the ferromagnetic material is so readily isolated from the biological processes occurring at the particles.

Methods in which an aqueous solution of a precursor of the magnetic material is emulsified in the water-immiscible liquid. The particles comprise a discrete core of magnetic material coated with a metal oxide, in which the coating typically weighs from 5 to 50% of the core. New particles generally have diameters in the range 5 microns and less, particularly in the range 0.1 to 2 microns. These may have a somewhat irregular shape or a smooth spherical shape.

The magnetically attractable particles of this invention may be coupled to biological or organic molecules with affinity for or the ability to adsorb certain other biological or organic molecules. Particles so coupled may be used in a variety of in vitro or in vivo systems involving separation steps or directed movement of coupled molecules to specific sites. Application include, but are not limited to immunological assays, other biological assays, biochemical or enzymatic reactions, affinity chromatography, cell sorting and diagnostic and therapeutic uses.

These particles can be used as supports for immobilized enzymes, antibodies, antigens and other bioactive materials. The current practice, for example, In the industrial production of lactose-free milk is to add the enzyme $\beta$-galactosidase to milk in a conventional stir bank reactor and then allow a specific reaction to take place. Following this the milk is pasteurized which destroys the enzyme in the process. On the other hand if the enzyme were immobilized on a magnetic particle, such as provided by this invention, it could be recovered by a magnetic separation and reused. The process of this invention is capable of producing coated particles having cores of a ferrite composition which have little or no tendency to retain a residual magnetism. Hence any re-use would not result in particle aggregation which is associated with ferrous materials due to retained magnetic properties of the ferromagnetic composition. The use of these magnetic particles in such a process significantly improves the economics of the process.

Other considerations include new therapies which have been developed for the treatment of diseases, such as childhood leukemia. Current experimental treatments include the use of magnetite, impregnated polystyrene beads which are coated with bioactivations. Biomaterials specifically recognize and bind to the surface of the leukemic cells thus allowing the separation of diseased and healthy cells. The healthy cells are reintroduced into the patient after all of his/her remaining bone marrow cells have been destroyed through aggressive chemotherapy. The problem with the existing technology is that the magnetic particles currently used in this type of therapy are quite large, that is, in the range of 5 micrometers or more. Unfortunately, smaller particles of this composition are ineffective due to surface roughness. On the other hand, the coated ceramic particles of this invention are smooth and small for this application, that is, in the range of 1 to 2 micrometers and will overcome the problems of the larger, rougher, magnetic impregnated beads.

The particles produced according to this invention, are also useful in diagnostic test. For example, in the examination of blood, there are usually several centrifugation steps involved to separate the various fractions including cells, platelets, serum and plasma. If magnetic particles coated with the appropriate immobilized bioactive materials were used, virtually all centrifugation steps could be eliminated which opens the way for the development of rapid automated blood diagnostic equipment. This would considerably lower costs of the diagnosis and increase the speed of testing.

The following Examples illustrate the invention.

EXAMPLE 1

49.5 g $FeCl_2.4H_2O$ and 202.4 g $Fe(NO_3)_3 9H_2O$ were added to 250ml and 50ml of distilled water respectively, and stirred until dissolved. The solutions were combined and added to 4.2 l of aqueous $NH_3$ to precipitate the hydrous $Fe_3O_4$, which was washed with water to remove any salts. The progress of the washing was monitored by measuring the conductivity of the supernate and was considered to be complete when the conductivity <1 mmhO. The precipitate was centrifuged yielding 86 g and was shown to contain 25 w/o $Fe_3O_4$ by gravimetric analysis.

73 g of the $Fe_3O_4$ paste prepared above was dispersed into 54 ml 370 gl$^{-1}$ $ZrO_2$ sol using a high shear mixer. 100 ml of distilled water was required to reduce the viscosity to an acceptable level. 50 ml of this mixture was added to 150 ml of an immiscible organic solvent containing a surfactant (2.8 w/o Span 80/Genklene), and was dispersed to micron sized droplets using the high shear mixer. After 1 minute $NH_3$ gas was used to gel the microspheres. The particles were then dewatered and calcined at 400° C.

The obtained particles were subjected to magnetic fields ranging from +10000 Oe to −10000 Oe. The maximum extent of magnetization of the particles was 37 e.m.u. per gram. A graph was drawn of magnetization (expressed as a proportion of the maximum possible) against applied magnetic field. The graph was a single line passing through the origin; no hysteresis loop was observed. This demonstrates that the particles are superparamagnetic, and that they do not retain magnetization when the magnetic field is removed.

As predicted from the results in the previous paragraph, these particles were readily brought down out of aqueous dispersion by application of a magnetic field and were readily re-dispersed after removal of the magnetic field.

Leaching tests carried out by mixing the particles for 14 hours in an aqueous medium buffered to pH3 and 11 showed iron concentrations of 720 ppm and 0 ppm respectively (corresponding to the leaching of 4% and 0% of the iron contained in the magnetic core). Such concentrations are significantly Lower than those found from commercially available magnetic particles e.g. 4000 ppm and 3 ppm respectively.

EXAMPLE 2

Zirconia-coated magnetic particles.

By techniques described in example 1, particles containing 10%, 25%, 50% and 90% of $Fe_3O_4$, were prepared. Scanning electron microscopes pictures of sections of the particles showed the following:

At 10% and 25% loading, the mass of finely divided $Fe_3O_4$ formed a rather tight core, completely encapsulated in oxide, with no magnetic material detectable at the particle surface.

At 50% loading, the mass of finely divided $Fe_3O_4$ formed a rather looser core, but nevertheless with a surrounding layer of oxide, and little or no magnetic material being detectable at the particle surface.

At 90% loading, the mass of finely divided $Fe_3O_4$ was concentrated towards the centre of the particle, but an appreciable portion was detectable at the surface.

Pore size determination confirmed that, at 50% loading, the proportion of $Fe_3O_4$ on the particle surface was negligible.

EXAMPLE 3

Mixed $ZrO_2/TiO_2/Fe_3O_4$.

3g of $ZrO_2$ sol (oxide equivalent) prepared as per GB 1412937 (1975) was higher-shear mixed with 4g of a 0.4 micron nomina size $TiO_2$ powder (research powder from Tioxide Ltd.) for 5 minutes. 3g of a wet, hydrated $Fe_3O_4$ powder, prepared by conventional co-precipitation techniques was subsequently added, and the mix high shear mixed for a further 5 minutes. Total volume was 40 ml.

The mixture was added to 150ml of Genklene (1,1,1,-trichloroethane) / 1% sorbitan monooleate (Span 80) and the emulsion high shear mixed at 8500 r.p.m. for 15 minutes. The spherical particles were subsequently gelled using ammonia ($NH_3$) gas until complete gelation occurred. The particles were dewatered and calcined at 400° C.

The product consisted of spheres of a mixed composition $ZrO_2/TiO_2$ with a magnetic core. Typical size range was 2-3 microns with excellent sphere quality type, a narrow particle size distribution and good mechanical strength.

EXAMPLE 4

Mixed $TiO_2/TiO_2/Fe_3O_4$.

This was prepared as Example 3 using 3g $TiO_2$ sol, 4g $TiO_2$ 0.4 microns passenger (Tioxide Ltd.) and 3g $Fe_3O_4$. The mix was added to 150ml of Span/Genklene and was stirred at 300 r.p.m. for 15 minutes. The spherical particles were subsequently gelled using $NH_3$ gas until gelation was complete.

The product was a porous $TiO_2$ particle with a magnetic core. Typical size was around 50–60 microns with good sphere quality, narrow size distribution and good mechanical strength.

EXAMPLE 5

Mixed $TiO_2/TiO_2/Fe_3O_4$.

This was performed as in example 4, but the Span/Genklene/powder mix was high shear mixed at 8500 r.p.m. The product was a 2-3 micron particle with good sphere quality, a narrow size distribution and good mechanical strength.

EXAMPLE 6

Mixed $Fe_2O_3/Fe_3O_4$.

A slurry of 4.28g $Fe_3O_4$ was added to 62.5 ml of a 2M solution of $Fe(NO_3)_3$. The mixture was homogenized and dispersed in 300 ml of Genklene containing 5% Span 80. The dispersion was subjected to high shear for 5 minutes and then gelled by means of $NH_3$ gas. The particles were separated from the supernatant liquid, washed with acetone, water and ether, and fired at 400° C.

EXAMPLE 7

Alumina-Coated Magnetic Particles

A precursor salt solution was made up of ferric nitrate and lithium nitrate in distilled water in a proportion that would result in lithium ferrite, $LiFe_5O_8$, after drying and decomposition, the solution comprising 1010-g/L Fe $(NO_3)_3.9H_2O$ and 34.5 g/L $LiNO_3$. A sol of colloidal pseudoboehmite was prepared by techniques well known in the art of sol-gel techniques, peptized with nitric acid and treated with sodium dodecyl sulfate. This sol was transferred into the salt solution in proportion that would result in a ratio $Al_2O_3/LiFe_5O_8$ of 0.05.

The resulting sol solution was then emulsified in n-heptane, the emulsion consisting of 30% by volume of the aqueous solution, 70% by volume of n-heptane and including 5% by volume of Span 80 as a surfactant and using a Brinkmann homogenizer as an emulsator. Ammonia gas was then bubbled through the emulsion until the pH had increased to about 10 to 11. The water and heptane were removed by spray drying and the resulting powder was calcined at 700° C. for 2 hours to result in an unagglomerated magnetic powder size distribution 0.1 to 0.5 micrometers. The TEM photomicrograph of the powder indicates that the particles are relatively irregular in shape. The thickness of the alumina coating is, however, relatively uniform at 10 to 20 nanometers.

EXAMPLE 8

Zirconia-Coated Magnetic Particles

A precursor salt solution was made up nickel nitrate, zinc nitrate and ferric chloride in distilled water in a proportion that would result in nickel zinc ferrite, $Ni_{0.38}Zn_{0.64}Fe_2O_4$, after drying and decomposition. The solution was mixed with a sol of zirconium oxide suspended in acetic acid solution obtained from Nyacol Product Inc. in a proportion that would result in a ratio $ZrO_2/Ni_{0.38}Zn_{0.64}Fe_2O_4$ of 0.20.

The resulting sol solution was then emulsified, reacted with ammonia, dried and calcined as done in the previous example. Examination of the powder under SEM indicate that the particles obtained are spheres of diameter varying between 0.5 to 0.8 micrometers.

Leaching tests carried out by mixing the particles in 1N nitric acid solution for 24 hours indicate that the zirconia coating is very effective in protecting the magnetic core since no detectable dissolution of the iron could be measured.

EXAMPLE 9

Alumina-Coated Magnetic Particles

In Examples 7 and 8, the sol was added before emulsification of the salt solution. In the present example, this procedure was modified as the alumina was added to the emulsified salt solution; the solution containing zinc nitrate, nickel nitrate and ferric chloride was emulsified in n-heptane, and treated with ammonia until the pH had increased to 10 to 11. The reacted-emulsion was diluted with fresh heptane, mixed and settled and the supernatant heptane was then removed. Such a washing procedure was repeated 3 times. The emulsion was then dewatered using a "Dean Stark" dewatering trap. It was then washed as described previously, settled for 1 day and the supernatant heptane removed. An alumina sol, similar to that of Example 11, in which 4% by volume of Tween 80/Span 80 mix adjusted proportion to obtain a HLB value of 13.0 had been added, was transferred into the emulsion In proportion that would result in a ratio $Al_2O_3/Ni_{0.36}Zn_{0.64}Fe_2O_4$ of 0.20. The mix was ultra-sonically dispersed and then emulsified again in n-heptane in the ratio by volume of 50%, using 2% by volume of Span 80 as the surfactant. The water was subsequently removed by refluxing the emulsion in the dewatering trap. After the removal of the organic phase In the spray drier, the powder was calcined at 700° C. for 2 hours. The calcined powders that resulted had a particle size in the range less than 1 micrometer, were spherical with a core of magnetic lithium ferrite in an alumina shell.

Leaching tests showed that the amount of iron dissolved after 24 hours immersion in 1N nitric acid solutions was 0.55 ppm $Fe_2O_3$. Such an amount corresponded to the dissolution of less than 0.1% of the total $Fe_2O_3$ contained in the ferrite core.

The specific amount of proteins (i.e. prothromb bound on the particles after Immersion for a period of 15 minutes in a Tris HCl buffer solution at pH of 7.4 was determined to be 0.57 $\mu$g per unit surface area of the particles ($cm^2$). Such an amount compares very favourably to that obtained under the same experimental conditions for other supports available on the market e.g. 0.47 $\mu g/cm^2$ for polystyrene surfaces and 0.33 $\mu g/cm^2$ for PVC surfaces.

We claim:

1. A method of making magnetically attractable particles by the use of:
    a) a precursor salt solution or sol or dispersion of magnetic material,
    b) a precursor salt solution or sol of a coating inorganic oxide, and
    c) an inert liquid immiscible with an aqueous solvent used in a) and b),
    which method comprises emulsifying a) and b) either together or separately in c), converting droplets of the emulsion to a gel, and heating the resulting gel droplets to form magnetically attractable particles comprising the magnetic material encapsulated in the coating inorganic oxide.

2. A method as claimed in claim 1, wherein the magnetic material of a) is dispersed throughout the solution or sol b) and the resulting mixture in then emulsified in c).

3. A method as claimed in claim 2, wherein a particulate non-magnetic refractory oxide is also dispersed in the solution or sol b).

4. A method as claimed in claim 1, wherein a solution of the magnetic material precursor a) is mixed with the solution or sol b) and the resulting mixture is then emulsified in c).

5. A method as claimed in claim 1, wherein a solution of the magnetic material precursor a) is emulsified in c) and the droplets of the emulsion converted to a gel, then the resulting gel droplets are dispersed in the solution or sol b), and the resulting mixture is emulsified In c), the droplets of the emulsion are converted to a gel, and the resulting gel droplets are heated to form the water dispersable magnetically attractable particles.

6. A method as claimed in claim 5, wherein the solution or sol b) containing the dispersed gel droplets is emulsified in c) in the presence of a surfactant having an HLB number greater than 10.

7. A method as claimed in claim 1, wherein the magnetic material is superparamagnetic.

8. A method as claimed in claim 1, wherein the magnetic material is a "soft" magnetic material.

9. A method as claimed in claim 1, wherein the magnetic material has a low Curie temperature.

10. A method as claimed in claim 1, wherein ammonia or an amine is added to the emulsion to convert aqueous droplets thereof to a gel.

11. A method as claimed in claim 1, therein the gel droplets are heated at a temperature of 250–2000° C.

* * * * *